United States Patent

Kensey et al.

[11] Patent Number: 5,935,147
[45] Date of Patent: *Aug. 10, 1999

[54] HEMOSTATIC PUNCTURE CLOSURE SYSTEM AND METHOD OF USE

[75] Inventors: Kenneth Kensey, Chester Springs; John Nash; Douglas Evans, both of Downington, all of Pa.

[73] Assignee: Kensey Nash Corporation, Exton, Pa.

[*] Notice: This patent is subject to a terminal disclaimer.

[21] Appl. No.: 08/992,041

[22] Filed: Dec. 17, 1997

Related U.S. Application Data

[63] Continuation of application No. 08/604,205, Feb. 21, 1996, Pat. No. 5,707,393, which is a continuation of application No. 08/426,371, Apr. 21, 1995, which is a continuation of application No. 08/154,882, Nov. 18, 1993, Pat. No. 5,441,517, which is a continuation of application No. 07/846,322, Mar. 5, 1992, Pat. No. 5,282,827, which is a continuation-in-part of application No. 07/789,704, Nov. 8, 1991, Pat. No. 5,222,974.

[51] Int. Cl.⁶ .................................................. A61B 17/08
[52] U.S. Cl. ............................................ 606/213; 606/232
[58] Field of Search .................................. 606/213, 232, 606/144, 139, 148; 604/60

[56] References Cited

U.S. PATENT DOCUMENTS 4,890,612  1/1990  Kensey ........................................ 606/213
5,350,399  9/1994  Erlebacher et al. ......................... 606/213
5,451,235  9/1995  Lock et al. .................................. 606/213

*Primary Examiner*—Michael Buiz
*Assistant Examiner*—Tina T. D. Pham
*Attorney, Agent, or Firm*—Caesar, Rivise, Bernstein, Cohen & Pokotilow, Ltd.

[57] ABSTRACT

A system, a closure, and method of use for sealing a percutaneous puncture in a blood vessel. The puncture includes an opening in the vessel wall and a tract leading to the opening. The system includes an introducer sheath and associated positioning device, a hemostatic puncture closure, and a deployment instrument. The positioning device enables the introducer sheath to be positioned at a desired position within the vessel. The deployment instrument includes a tubular carrier storing the closure. The closure comprises a rigid, e.g., radio-opaque, anchor, a compressed collagen plug, and a thin filament connecting the two in a pulley-like arrangement. The instrument and introducer are used to introduce the closure into the puncture, with the anchor located within the artery and with the collagen plug within the puncture tract. A locking member is provided to hold the closure in place at its operative position, whereupon hemostasis occurs rapidly, thereby sealing the puncture.

18 Claims, 11 Drawing Sheets

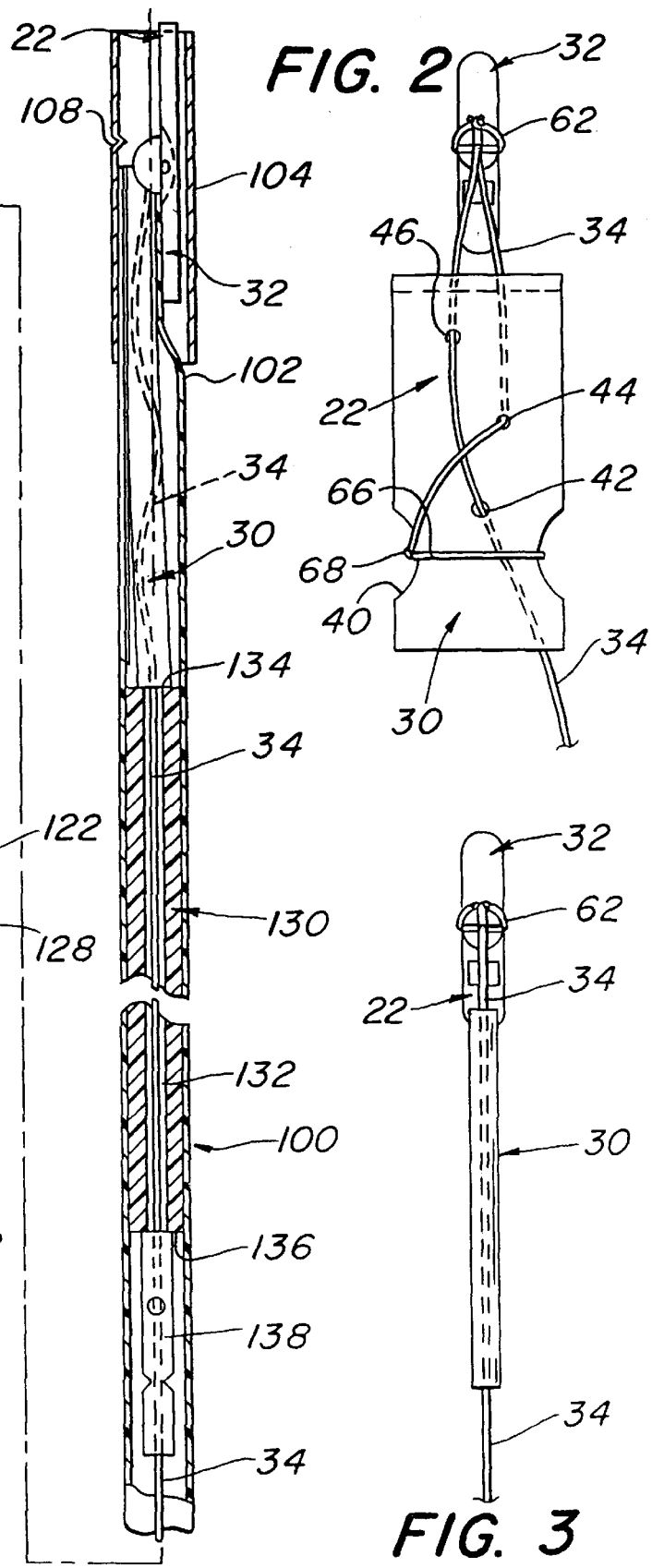

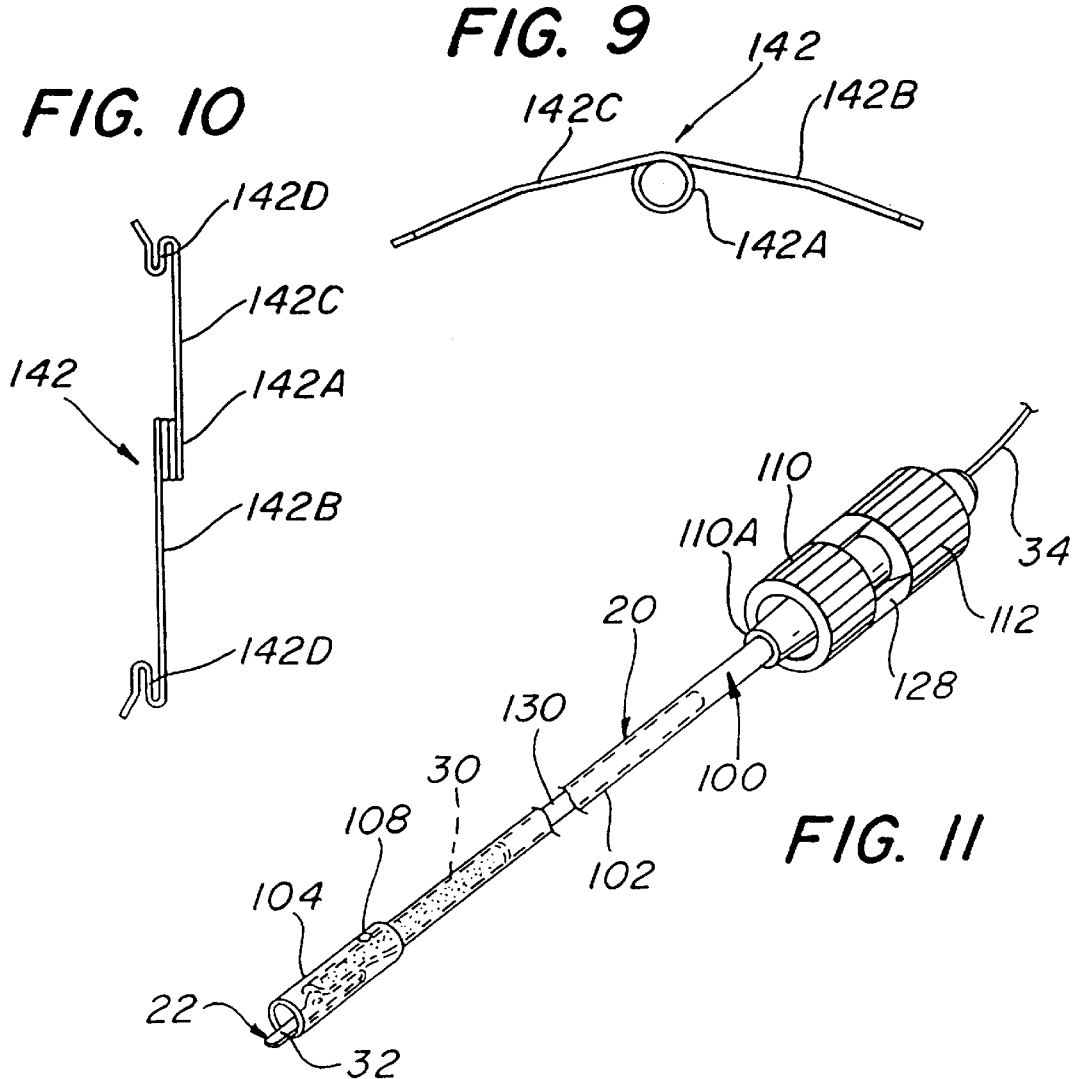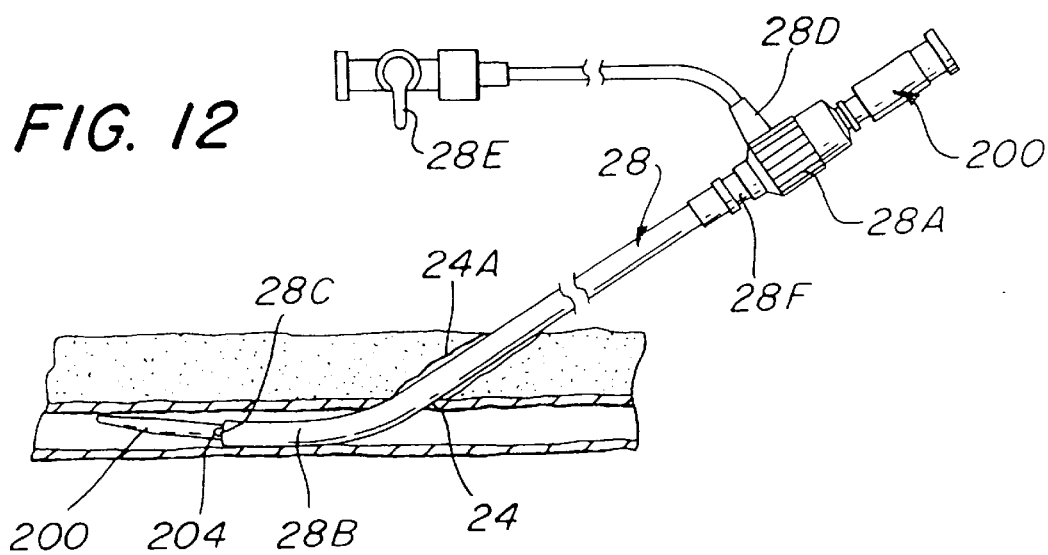

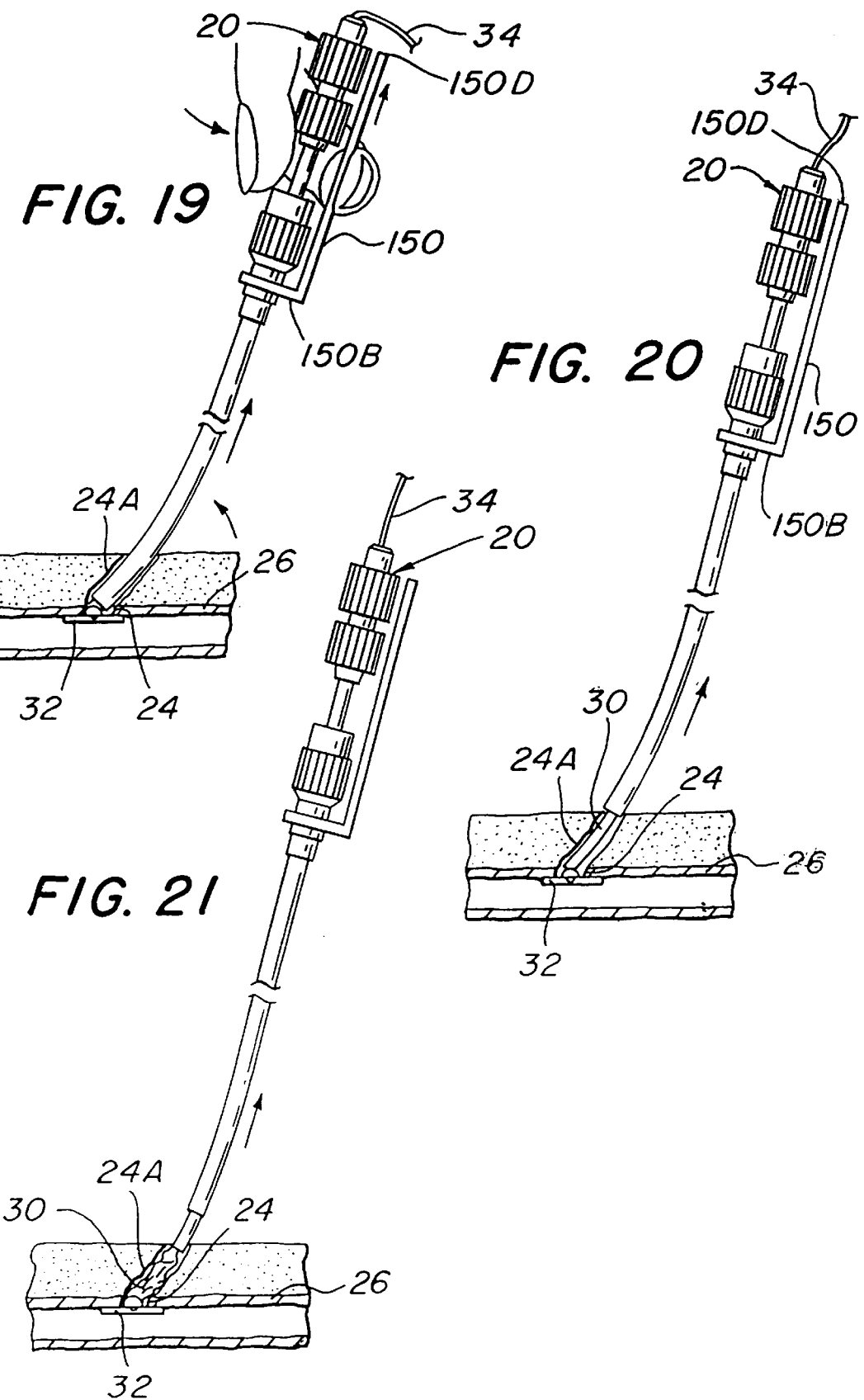

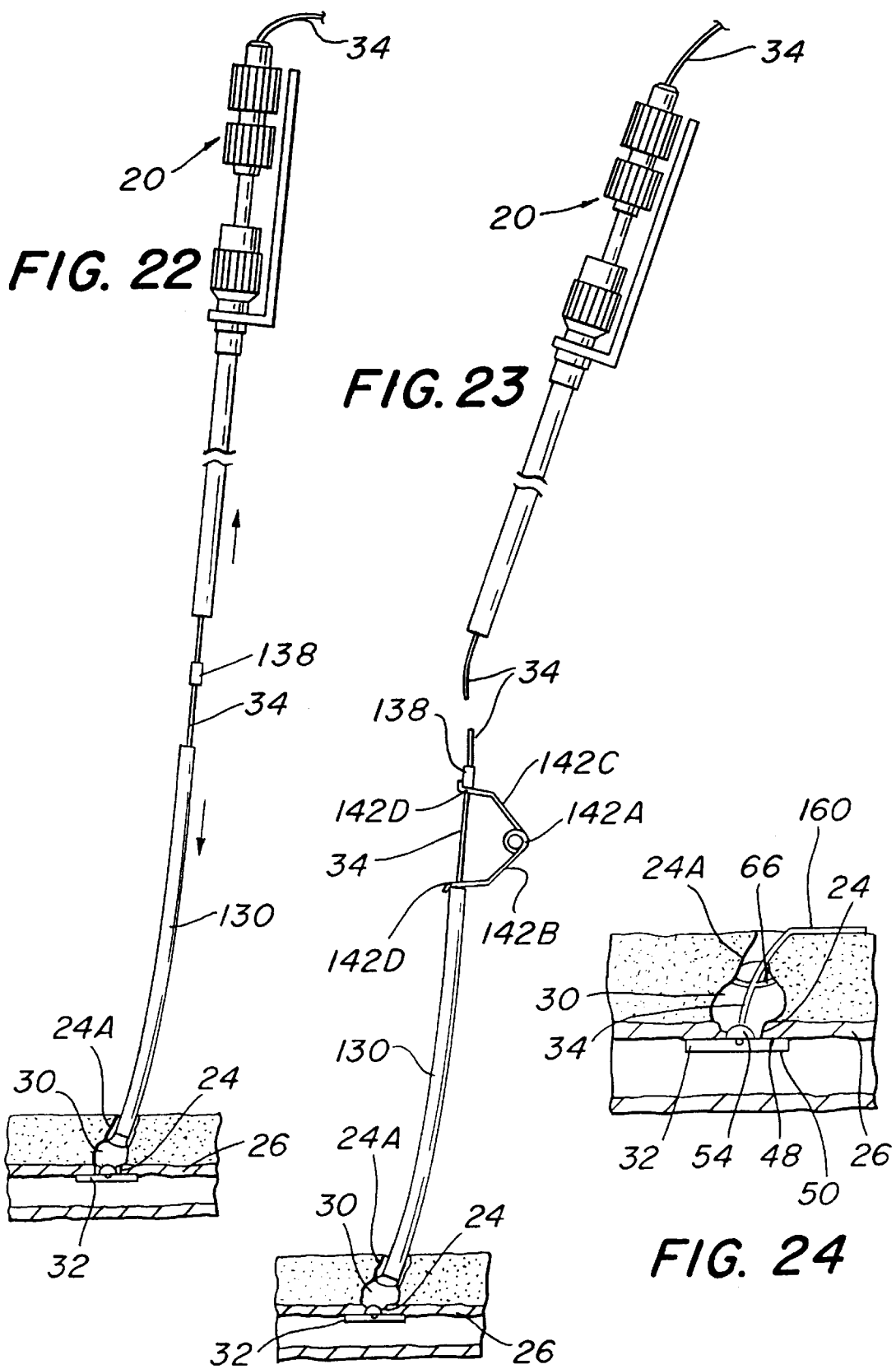

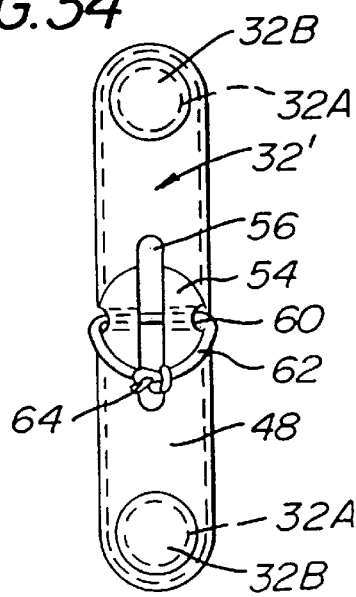
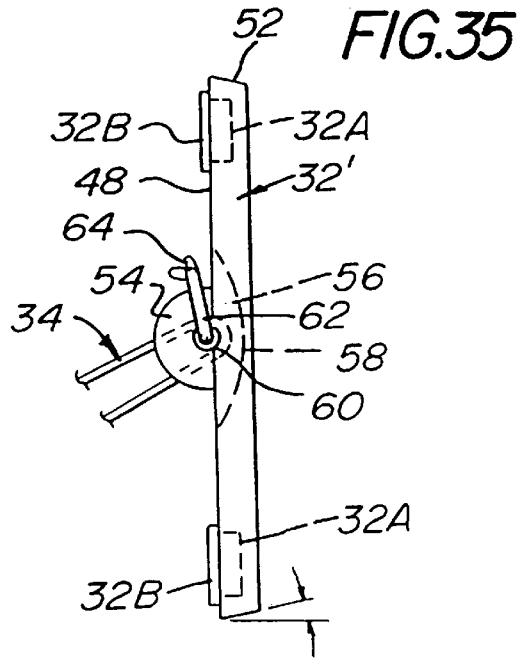
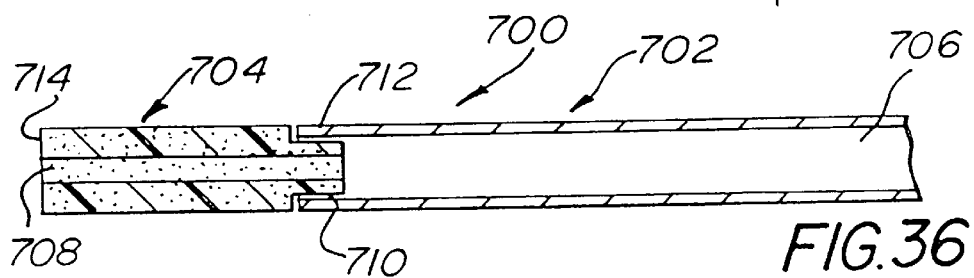
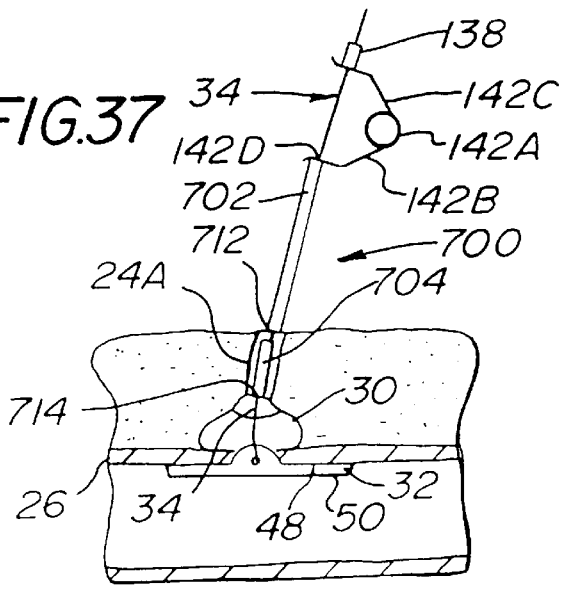
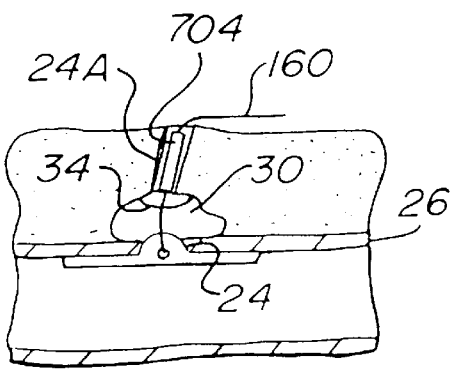

HEMOSTATIC PUNCTURE CLOSURE SYSTEM AND METHOD OF USE

SPECIFICATION

This application is a Continuation of our earlier filed U.S. patent application Ser. No. 08/604,205 filed on Feb. 21, 1996 entitled Hemostatic Puncture Closure System and Method of Use, now U.S. Pat. No. 5,707,393, which in turn is a Continuation of our earlier filed U.S. patent application Ser. No. 08/426,371 filed on Apr. 21, 1995 entitled Hemostatic Puncture Closure System and Method of Use, which in turn is a Continuation of our earlier filed U.S. patent application Ser. No. 08/154,882 filed on Nov. 18, 1993, entitled Radioopaque Hemostatic Puncture Closure System and Delivery System Therefore, now U.S. Pat. No. 5,441,517, which in turn is a Continuation of our earlier filed U.S. patent application Ser. No. 07/846,322 filed on Mar. 5, 1992, entitled Hemostatic Puncture Closure System and Method of Use, now U.S. Pat. No. 5,282,827, which in turn is a Continuation-In-Part of our earlier filed U.S. patent application Ser. No. 07/789,704, filed on Nov. 8, 1991, entitled Hemostatic Puncture Closure System and Method of Use, now U.S. Pat. No. 5,222,974, all of whose disclosures are incorporated by reference herein and which are assigned to the same assignee as this invention.

BACKGROUND OF THE INVENTION

In U.S. Pat. No. 5,021,059, which has been assigned to the same assignee as this invention, there is disclosed a closure device and method of use for sealing a small incision or puncture in tissue separating one portion of the body of a living being from another portion thereof, e.g., a percutaneous puncture in an artery, to prevent the flow of a body fluid, e.g., blood, through the puncture. The closure device is arranged to be used with (deployed by) an instrument which comprises a carrier in the form of a tubular member. The tubular member has a proximally located portion and a distally located portion. The latter includes an open free end arranged to be introduced through the incision or puncture. The proximately located portion of the tubular member is arranged to be located out of the body of the being when the distally located portion is extended through the incision or puncture.

The closure device comprises three components, namely, an anchor member, a sealing member, and a filament, e.g., suture. The sealing member is formed of a hemostatic material, e.g., compressed collagen foam. The anchor member includes a tissue engaging portion configured to pass through the puncture in one direction but resistant to passage therethrough in the opposite direction. The sealing member includes a tissue engaging portion. The filament is connected between the anchor member and the sealing member in a pulley-like arrangement so that they may be moved relative to each other by the application of a pulling force on the filament.

The instrument is arranged to expel the anchor member through the puncture, e.g., into the artery, and to draw its tissue engaging portion into engagement with the tissue contiguous with the puncture. The filament extends through the instrument to a point outside the body of the being and is arranged to be drawn in the proximal direction, whereupon the portion of the filament connecting the anchor member and the sealing member causes the tissue engaging portion of the sealing member to move with respect to said anchor member and into engagement with the tissue contiguous with the puncture on the opposite side thereof from said anchor member. This action causes the tissue engaging portion of the sealing member to seal the puncture from the flow of fluid therethrough.

The closure device and deploying instrument in that patent leave something to be desired from the standpoints of effectiveness and efficiency of use.

OBJECTS OF THE INVENTION

Accordingly, it is a general object of this invention to provide a closure device and methods of use which overcomes the disadvantages of the prior art.

It is a further object of this invention to provide a system including a closure, a deploying instrument, and method of use for quickly, easily, safely and effectively sealing a percutaneous puncture in a blood vessel within the body of a living being from another portion.

It is still a further object of this invention to provide devices and methods for enabling one to radiographically image the closure during its placement to seal a percutaneous incision or puncture in a blood vessel and after such placement has been accomplished.

SUMMARY OF THE INVENTION

These and other objects of this invention are achieved by providing a closure for use in a system for sealing a percutaneous incision or puncture in a blood vessel. The system basically comprises carrier means, introducer means, and closure means. The puncture comprises a tract extending through tissue overlying the blood vessel. The closure means comprises anchoring means, sealing means, and filament means. The filament means is connected between the anchoring means and the sealing means. The introducer means comprises a tubular member having a distal free end arranged to be inserted into the puncture tract and through the puncture. The carrier means is arranged to be inserted through the introducer means to expel the anchoring means therefrom and to draw the anchoring means into engagement with the distal free end of the introducer means. The introducer means and the carrier means are arranged to be moved together to draw the anchoring means into engagement with the interior tissue of the blood vessel contiguous with the puncture. The filament means is arranged to pull the anchoring means and the sealing means relative to each other to cause the sealing means to engage tissue contiguous with the puncture outside of the vessel.

In accordance with one aspect of this invention the system includes means and a method of use to enable one to readily determine the location of the wall of the vessel or lumen by the percutaneous introduction of such means into the vessel or lumen. Such means can be used as a part of the system or method to seal the puncture or incision in a vessel or lumen or may be used for other purposes, e.g., it may be used for any application wherein it is desirable to determine the location of a vessel or lumen wall via a percutaneous incision or puncture.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 1 is a side elevational view, partially in section, showing a deploying instrument and a closure device of the system of the subject invention;

FIG. 2 is an enlarged top plan view of the closure device shown in FIG. 1, with the sealing component shown in an uncompressed state;

FIG. 3 is a top plan view, like that of FIG. 2, but showing the sealing component in its compressed state ready for deployment by the instrument of FIG. 1;

FIG. 9 is a front elevational view of a torsion spring used with the deployment instrument;

FIG. 10 is a side elevational view of the spring shown in FIG. 9;

FIG. 11 is an isometric view of the deployment instrument shown in FIG. 1;

FIG. 12 is an illustration showing a preliminary step in the positioning of a conventional introducer sheath through a percutaneous puncture in an artery using the position indicating device shown in FIG. 7;

FIGS. 15–23 are illustrations, similar to FIGS. 11 and 12, but showing the sequential steps in the use of the instrument to deploy the closure device to seal the percutaneous puncture in the artery;

FIG. 24 is an enlarged illustration showing the closure device in place after it has sealed the percutaneous puncture in the artery;

FIG. 34 is an enlarged top plan view of an alternative anchor component to that shown in FIG. 4;

FIG. 35 is an enlarged side elevational view of the alternative anchor shown in FIG. 34;

FIG. 36 is an enlarged sectional view of an alternative tamping means to that shown in FIG. 1;

FIG. 37 is an enlarged illustration similar to FIG. 23 but showing the use of the alternative tamping means of FIG. 36; and FIG. 38 is an enlarged illustration similar to FIG. 24 but showing the closure device in place after it has sealed the percutaneous puncture in the artery using the alternative tamping means.

DETAILED DESCRIPTION OF THE PREFERRED EMBODIMENT

Figure 4:
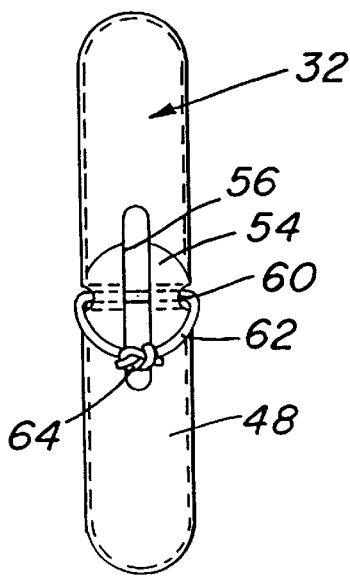
FIG. 4 is an enlarged top plan view of the anchor component of the closure device.

Referring now in greater detail to the various figures of the drawings wherein like reference characters refer to like parts, there is shown at 20 an instrument forming a portion of a system for deploying a closure device 22 to seal a percutaneous puncture 24 within a blood vessel 26, e.g., the femoral artery, constructed in accordance with this invention. The puncture 24 includes not only the opening in the wall of the vessel but also the tract 24A, i.e., the passageway in the tissue located between the vessel and the skin of the being formed when the vessel is punctured.

The instrument 20 and closure device 22 have particular utility when used in connection with intravascular procedures, such as angiographic dye injection, cardiac catheterization, balloon angioplasty and other types of recanalizing of atherosclerotic arteries, etc. since the closure 22 is designed to cause immediate hemostasis of the blood vessel, e.g., arterial, puncture. However, it is to be understood that while the description of the preferred embodiment instrument and closure contained herein is directed to the closing off of percutaneous incisions or punctures in arteries, they have much more wide-spread applications. Thus, the sealing of a percutaneous opening in an artery shown herein is merely exemplary.

Before describing the closure 22 and the instrument 20 for inserting it to seal the opening, a brief description of a typical, conventional, intravascular surgical procedure, e.g., catheter instrumentation of an artery, utilizing a percutaneous opening will be given to best appreciate the features of the invention. In such a procedure a cannula of an instrument, such as an angiographic needle (not shown), is inserted percutaneously through the skin into the artery, such as the femoral artery, at the situs for the instrument's insertion. The needle cannula is held in place and the flexible end of a mini-guidewire (not shown) is then passed through the cannula into the artery to the desired depth (i.e., longitudinal position therealong). Once the mini-guide wire is in place the needle cannula is removed, leaving the guidewire in place. An introducer sheath 28 (FIGS. 12 and 13) and an arterial dilator (not shown) are then passed over the guidewire, through the puncture or incision and into the artery. The guidewire and then the dilator are removed leaving the introducer sheath in place. A catheter, or other intravascular instrument (not shown) is then inserted through the introducer sheath 28 and threaded down the artery 26 to the desired intravascular location, e.g., the situs of the atherosclerotic occlusion.

Once the intravascular procedure (e.g., angioplasty) has been completed, the catheter is removed. Thereafter, the sheath is removed and the surgeon or other trained person applies manual, digital pressure to the percutaneous puncture until hemostasis has occurred. In particular, the current standard of care for puncture hemostasis is to apply digital or mechanical pressure on the puncture site for twenty minutes to an hour, depending on the puncture size and the degree of hemolytic therapy. Obviously this results in wasted time for the physicians and other catheter lab personnel, and causes inconvenience and discomfort for the patient. In addition serious complications arise from persistent bleeding and hematoma formation in approximately five percent of the patients.

In accordance with the method of this invention the introducer sheath 28 is left in place within the artery (although it is moved so that its distal end is at a desired position therein, as will be described later). The deployment instrument 20 having the closure device 22 therein is inserted into the introducer sheath. The closure device is then deployed (ejected) and operated to immediately seal the arterial puncture site 24 and plug the tract 24A. Moreover, as will be appreciated from the description to follow the closure device 22 is designed to reduce post-procedure puncture complications, cause minimal inflammatory reaction and resorb completely within a relatively short period of time, e.g., sixty to ninety days.

The details of the closure 22 and instrument 20 for introducing it will be described in detail later. Suffice it for now to briefly describe the closure and its method of deployment and use. Thus, as will be seen later the closure has three basic components, namely, a sealing member 30, an intraarterial anchor member 32, and a positioning member 34. The sealing member is in the form of an elongated rod-like plug, e.g., a hemostatic, resorbable collagen sponge or foam. This member is arranged for sealing the puncture. The anchor member 34 is an elongated, stiff, low-profile, resorbable member which is arranged to be seated inside the artery against the artery wall contiguous with the puncture 24. The anchor member 32 is made of non-hemostatic resorbable polymer similar to resorbable suture. The positioning member 34 comprises a filament, e.g., a resorbable suture. The suture connects the anchor member and the collagen plug (sealing member) via a pulley-like arrangement which serves to move the anchor and plug together, to sandwich and lock the artery wall between the anchor and plug.

The closure device 22 is used after the interventional procedure is finished. In particular, the physician inserts the delivery or deployment instrument 20 containing the closure device 22 into the patients' introducer sheath 28. On insertion, the anchor member 32 passes out of the distal end of the introducer sheath and deploys into the artery lumen. The deployment instrument 20 is then withdrawn from the introducer sheath until resistance is felt when the anchor member catches on the distal end thereof. Once this occurs (and assuming that the anchor is in the correct orientation when it catches on the end of the introducer sheath, as will be described later) the deployment instrument and the introducer sheath are then immediately withdrawn together. This withdrawing action causes the anchor member 32 to engage (catch) on the artery wall contiguous with the puncture. Continued withdrawal of the instrument and introducer sheath causes the pulley-like configuration of the filament to pull the collagen plug 30 toward the anchor member 32, thereby depositing the plug in the puncture tract 24A against the exterior of the artery contiguous with the puncture. The pulling on the filament to bring the plug into engagement with the puncture site also has the effect of deforming the plug into a larger diameter body to aid in holding it in place. Moreover, since the plug is formed of a compressed collagen it also expands automatically in the presence of blood within the puncture tract when deployed, thereby further contributing to the plug's enlargement. The instrument 20 also includes a tamper (to be described later) which is mounted on the suture and which is slidable thereon. The deployment of the plug member also effects the deployment of the tamper into the puncture tract proximally of the plug member. The tamper is then used to gently compress and lock the collagen plug on the outside of the artery.

The closure is now locked in place through the clotting of the hemostatic collagen plug and by spring tension (to be described later) on the filament 34 attached to the intraarterial anchor 32. Thus the artery wall is sandwiched between the collagen plug 30 and anchor 32. Within a few hours after deployment, the anchor 32 will be coated with fibrin and thus attached firmly to the arterial wall, thereby eliminating the possibility of distal embolization. After approximately thirty days, only a small deposit of anchor material will remain. In fact, resorption of all components will have occurred after approximately sixty days.

The anchor member 32 is non-hemostatic and is sized to be hemodynamically insignificant in comparison to the size of the femoral artery. Thus, the resorbable anchor has an insignificant hemodynamic effect on blood flow.

As will be appreciated by the description to follow deployment of the closure device 22 by the instrument 20 is easy, quick and reliable. Anchoring is repeatable, safe, and effective to deploy the collagen plug. Hemostasis occurs almost instantaneously, e.g., in 15 seconds or less, when the closure device is deployed properly.

Referring now to FIGS. 2–5 the details of the closure device 22 will now be described. As can be seen in FIG. 2 the sealing member or plug 30 comprises a cylindrical member formed of a compressible, resorbable, collagen foam, such as that sold by Collatec, Inc. of Plainsboro, N.J. The plug 30 is arranged to be compressed from the large diameter configuration shown in FIG. 2 to the small diameter, elongated configuration shown in FIG. 3. In the configuration of FIG. 3 the diameter of the plug is very small, e.g., 1.32 mm, and therefor suitable for disposition within the instrument 20 as will be described later. The plug 30 includes an annular recess 40 extending about its outer periphery adjacent its proximal end. Three apertures 42, 44, and 46 extend through the plug. In particular, the aperture 42 is located close to the recess 40 and diametrically through the centerline of the plug. The aperture 46 is located close to the distal end of the plug and extends transversely through the plug on one side of the centerline. The aperture 44 is located between apertures 42 and 44 and extends transversely through the plug on the other side of the centerline. These apertures serve as passageways through which the filament 34 extends to connect the anchor member to the plug and are spaced apart to preclude tearing of the plug.

The manner of connection of the plug to the anchor will be described later. Suffice it for now to state that the filament 34 of the closure device 22 serves to couple the plug component to the anchor component in an arrangement to effect the movement of the plug component toward the anchor component, once the anchor component is in its desired position in the artery at the puncture or incision. In particular the coupling of the plug component to the anchor component simulates a pulley to achieve a desired mechanical advantage.

In accordance with a preferred embodiment of this invention the filament is formed of resorbable, flexible, strong material, e.g., a resorbable suture.

Figure 5:
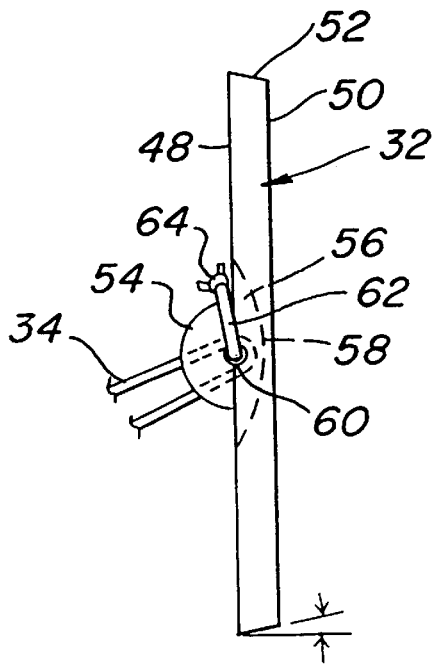
FIG. 5 is an enlarged side elevational view of the anchor component of closure device.

As can be seen in FIGS. 4 and 5 the anchor member 32 basically comprises a thin, narrow, strip or bar of material, such as a resorbable lactide/glycolide polymer sold by Medisorb Technologies International L.P. under the trade designation MEDISORB. The strip is sufficiently rigid such that once it is in position within the artery (as will be described later) it is resistant to deformation to preclude it from bending to pass back through the puncture through which it was first introduced. The member 32 has a generally planar top surface 48, a generally planar bottom surface 50 and a peripheral side surface 52. Each end of the member 32 is rounded. The side surface 52 of the anchor member 32 tapers inward from its top surface to its bottom surface as shown in FIG. 5 to facilitate the removal of the plug from the mold for making it. A hemispherical projection 54 is located at the center of the top surface 48. The hemispherical projection 54 includes a longitudinally extending slot 56 disposed perpendicularly to the top surface 48 of the member 32. The bottom 58 of the slot 56 is arcuate (FIG. 5). A cylindrical opening 60 extends transversely across the member 32 through the projection 54. A loop 62 of suture material extends through the opening 60. The loop 62 is closed by a knot 64. The portion of the loop 62 extending through the opening 60 overlies the bottom 58 of the slot and forms a "pin" about which the filament 34 extends. In particular the filament 34 is threaded through the slot 56, under the "pin" of the loop 60 and back out the slot 56 on the other side thereof as shown clearly in FIG. 5 to connect the plug member 30 to the anchor member 32.

Figure 6:
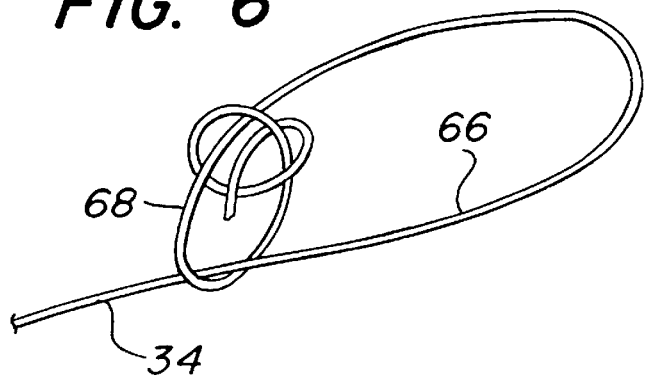
FIG. 6 is a greatly enlarged plan view showing the knot used to effect the securement of a filament component of the closure device to the sealing component thereof.

In this regard the pulley-like connection between the anchor member and the plug member is effected by threading the filament 34 from a remote point (which is located outside the deployment instrument 20 when the closure device is in place in that instrument) through the transverse aperture 42, down the plug to the aperture 46, through that aperture to the opposite side of the plug and from there to the anchor member where it is threaded through the slot 56 and about the "pin" as described earlier. From there the filament 34 extends back to the plug where it enters into aperture 44, passes through the aperture to the opposite side of the plug, where it terminates in a loop 66 extending around the annular recess 40. The loop is secured by a knot 68, whose details are shown in FIG. 6.

In FIGS. 34 and 35 there is shown an alternative anchor member 32'. That anchor member is virtually identical to the anchor member 32 except that member 32' includes means to enable it to be imaged radiographically to facilitate the placement of the closure at the desired situs within the patient's body. Thus, as can be seen therein the alternative anchor member 32' includes a pair of wells 32A in the top surface 48 adjacent the respective ends of the anchor member. A plug or powder of a conventional radio-opaque material, which is preferably biocompatible and which is excretable, e.g., solid agents of sodium diatrizoate, iohexal, etc., is located within each well 32A. A respective cover or cap 32B, preferably formed of a thin disk of a bioresorbable material, e.g., PGA, is disposed over each well to seal the material within the well. Each cover is secured to the top surface 48 of the anchor 32' by a seal line extending about the periphery of the well. That seal line can be formed in various ways, e.g., by heat sealing.

Referring now to FIGS. 1 and 11 the details of the deployment instrument 20 will now be described. As can be seen the instrument basically comprises a carrier 100 in the form of an elongated tube 102 formed of a somewhat flexible material, such as polyethylene or polyvinyl chloride, so that the carrier may be freely passed through the introducer sheath into an operative position within the patient's artery, notwithstanding any curvature of the introducer sleeve which may exist.

In accordance with a preferred embodiment of this invention the outside diameter of the tubular carrier 100 is 8 French. The distal end of the tube 102 includes a rigid, e.g., stainless steel, sleeve or bypass tube 104 mounted thereon, to enable it to be inserted through a conventional hemostasis valve 28A (FIGS. 12–14) forming a portion of the introducer sheath 28, through the sheath, and out the distal end thereof into the artery 26. The distal end of the flexible tube 102 necks down into a generally hemicylindrical configuration (See FIG. 1) which includes a longitudinally extending slit (not shown) therein to enable it to be fit within the bypass tube 104 without buckling.

As can be seen in FIG. 11, the closure device 22 is located within the distal end of the tubular carrier 100. In particular the anchor member 32 is disposed longitudinally within the bypass tube 104 laterally of the central longitudinal axis 106 of the carrier. The plug member 30 is located within the tube 102 just behind (proximally) of the anchor member and on the opposite side of the central longitudinal axis. In fact the distal end of the plug member overlies the proximal end of the anchor member. The bypass tube 104 includes a reference detent 108 in its periphery located diametrically opposite to the position of the anchor member. The detent 108 serves as a visual guide to help the user orient the instrument to a proper yaw angle with respect to the central longitudinal axis for insertion within the introducer sheath as will be described later.

As can be seen in FIGS. 1 and 11, the instrument 20 includes a conventional luer fitting 110. The proximal end of the carrier tube 102 extends into an opening in the fitting 110 and is secured in place therein by any suitable means. Another conventional luer fitting 112 is threadedly secured to the threaded distal end 114 of the fitting 110. The fittings 110 and 112 together form a hollow body through which the proximal end of the filament 34 extends. A tensioning assembly is located within that body and basically comprises a ball 116, a cup shaped ball seat 118, a compression spring 120, and a spring seat 122. The spring seat is a disk-like member located within an annular recess within the center of the luer fitting 110. The ball seat includes a conical inner surface 124 having a central opening 126. The spring is a helical member interposed between the spring seat 122 and the ball 116 to bias the ball toward the conical surface 124 of the ball seat 118. The proximally located portion of the filament 34 extends through the space between the ball 116 and its seat. The amount of force applied to the ball is established by a spacer sleeve 128 located between the luer fittings 110 and 112. By appropriate selection of the width of the sleeve 128 any desired preload can be applied to the spring.

As will be appreciated by those skilled in the art the tensioning assembly just described will tend to hold the filament in place with respect thereto until the force applied to the filament exceeds the preload force applied by the compression spring, whereupon the filament will be freed to slide through the instrument.

The carrier 100 also includes a tamping member 130. This member is an elongated rod-like member formed of any suitable material, e.g., polyethylene, and is disposed within the carrier tube 102 immediately proximally of the plug 32. The tamping member 130 includes a central passageway 132 extending down its length from its distal end 134 to its proximal end 136. The filament 34 portion extending from the anchor member 32 passes through the passageway 132 in the tamping member and from there into the luer fittings 110 and 112, past the tensioning assembly, and out through the hole 126 at the proximal end of the instrument 20. A holding sleeve or tag 138, e.g., a stainless steel tube, is crimped onto the filament so that it engages the proximal end of the tamping member 130 to hold that member in place. The tag 138 is arranged to cooperate with a torsion spring 142 (FIGS. 9 and 10) to apply tension onto the filament 34 after the closure device is in place to enable the instrument 20 to be removed and the filament severed (as will be described later).

Figure 13:
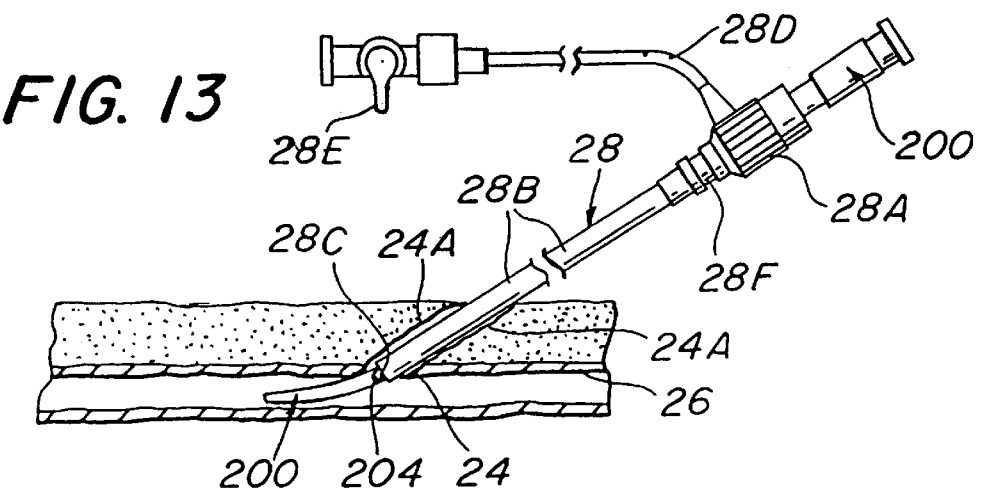
FIG. 13 is an illustration similar to that of FIG. 12 showing desired position of the introducer sheath within the artery as established by the use of the position indicating device shown in FIG. 7.
Figure 14:
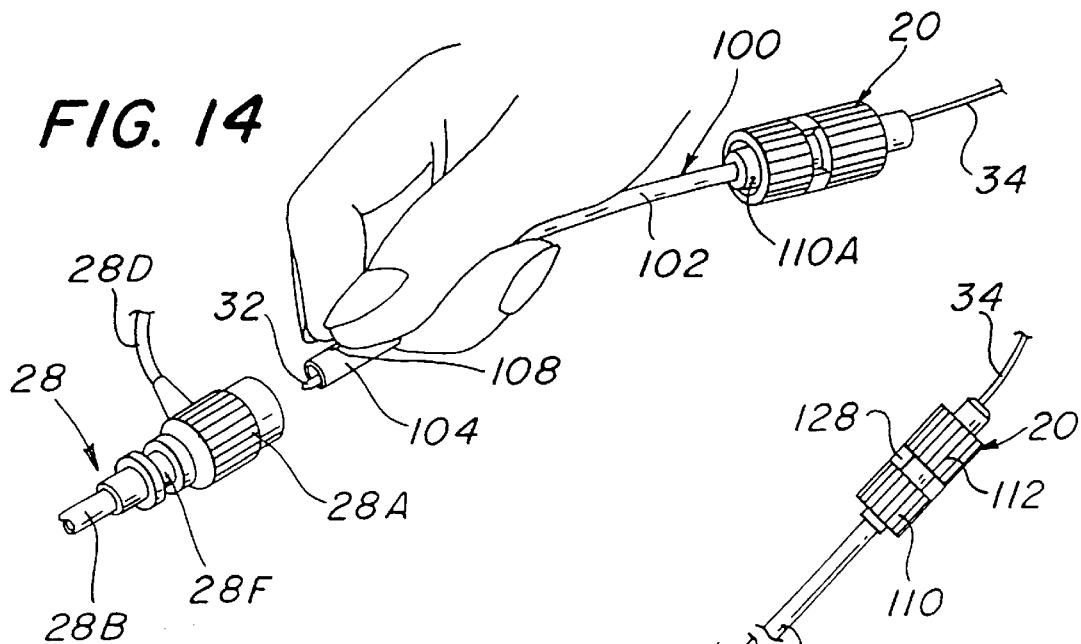
FIG. 14 is an illustration showing the introduction of the deployment instrument into the properly located introducer sheath.
Figure 15:
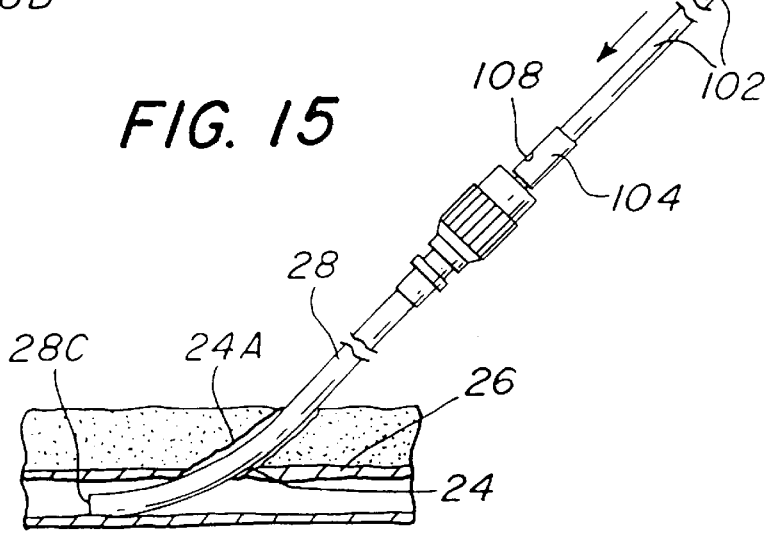
Figure 16:
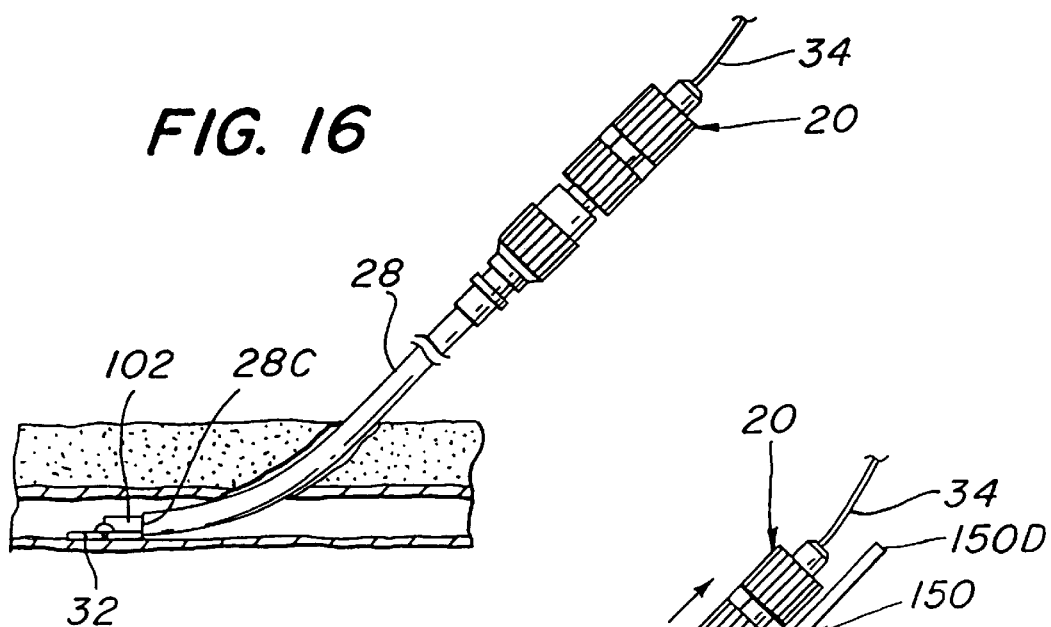

As mentioned earlier the instrument 20 is arranged to be inserted into a conventional introducer sheath 28 to effect the deployment of the closure device 20. Before describing that operation a brief description of the introducer sleeve and its method of location with respect to the percutaneous puncture is in order. As can be seen in FIGS. 12–14 the sheath 28 includes a body portion in which a conventional hemostasis valve 28A is located and a tubular portion 28B extending from the body. The tubular portion 28B terminates in an open distal or free end 28C. The body portion of the sheath 28 includes a sideport 28D having a conventional stopcock 28E located therein. The distal end of the body of the sheath includes an annular groove 28F which is arranged to receive a position indicator clip 150 forming a portion of the system of this invention, for reasons to be described later.

Figure 8:
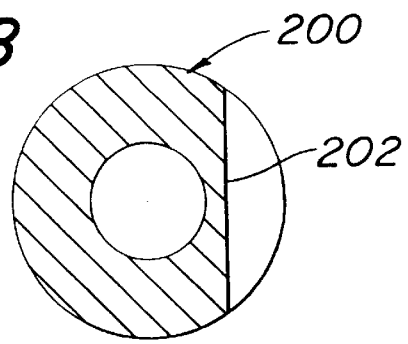
FIG. 8 is an enlarged sectional view taken along line 8—8 of FIG. 7.
Figure 7:
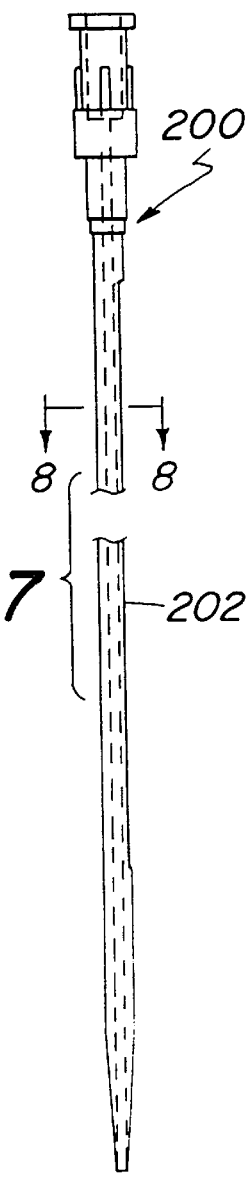
FIG. 7 is a top plan view of one embodiment of a introducer sheath position indicating device forming a portion of the system of this invention.

Before the instrument can be inserted into the introducer sheath 28, the sheath itself must be properly located within the artery. This action is accomplished via a positioning device 200. That device forms a portion of the system of this invention and is shown in FIGS. 7 and 8. As can be seen the device 200 basically comprises a conventional dilator whose outer periphery has been modified to include a longitudinally extending flat 202. The device 200 is arranged to be fully inserted within the introducer sheath 28 like shown in FIG. 12. The insertion of the device 200 within the introducer sheath 28 forms a passageway between the flatted surface 202 of the device 200 and the interior surface of the tubular portion 28B of the sheath disposed thereover. The length of the flatted portion 202 is selected so that when the device 200 is fully with the introducer sheath, and the distal end of the sheath within the interior of the artery, the distal end of the flatted surface extends just beyond the distal end 28C of the introducer sheath to form a window 204 into which blood may flow, while the proximal end of the surface 202 is in fluid communication with the interior of the introducer body and the sideport 28D. Accordingly, blood may flow into the window 204 through the passageway formed by the flatted surface, into the sideport 28D and from there to the stopcock 28E when the window 204 is within the interior of the artery.

In order to correctly position the introducer sheath the location of the artery wall must be established. This is accomplished by inserting the device 200 within the introducer sheath as just described and then opening the stopcock 28E to observe the flow of blood therefrom. The blood will normally flow out of the opened stopcock by virtue of the pressure differential across the lumen wall. If however, there is insufficient pressure to cause such a flow of blood some means (not shown) can be used to create the desired differential pressure, e.g., suction can be used. In any event once the flow of blood is observed the introducer sheath with the device therein is then retracted (moved proximally) until the blood flow through the stopcock just stops, a position shown in FIG. 13. This indicates that the distal end 28C of the introducer sheath has just left the artery lumen. The introducer sheath with the device therein is then reinserted approximately 10 mm into the puncture to ensure that the distal end of introducer sheath is at the desired position within the artery. Blood flow should be reestablished through the stopcock at this time. Then the stopcock is closed. From this point the introducer sheath must be kept fixed, i.e., it must not move axially relative to the patient. To achieve that end the user of the system should provide a continuous grasp on the introducer sheath, with the patient's groin as a position reference. The position indicating device 200 is then removed from the introducer sheath to ready the introducer sheath for receipt of the deployment instrument 20 carrying the closure device 22 as will be described later.

Figure 26:
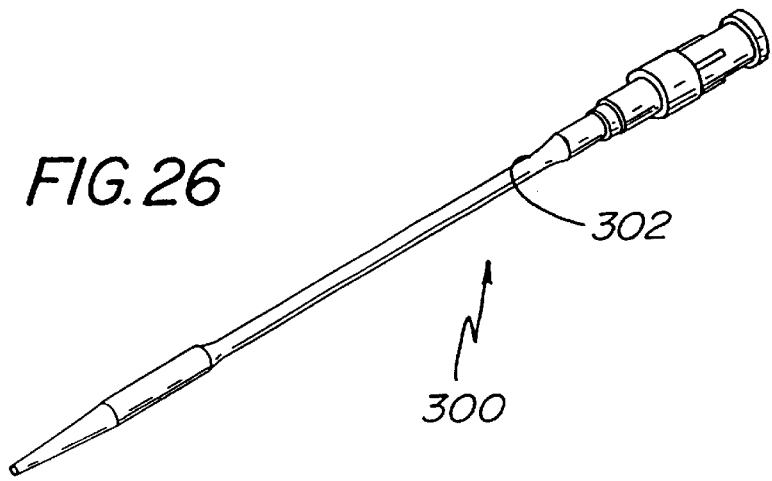
FIG. 26 is an isometric view of a second embodiment of a introducer sheath position indicating device forming a portion of the system of this invention.
Figure 27:
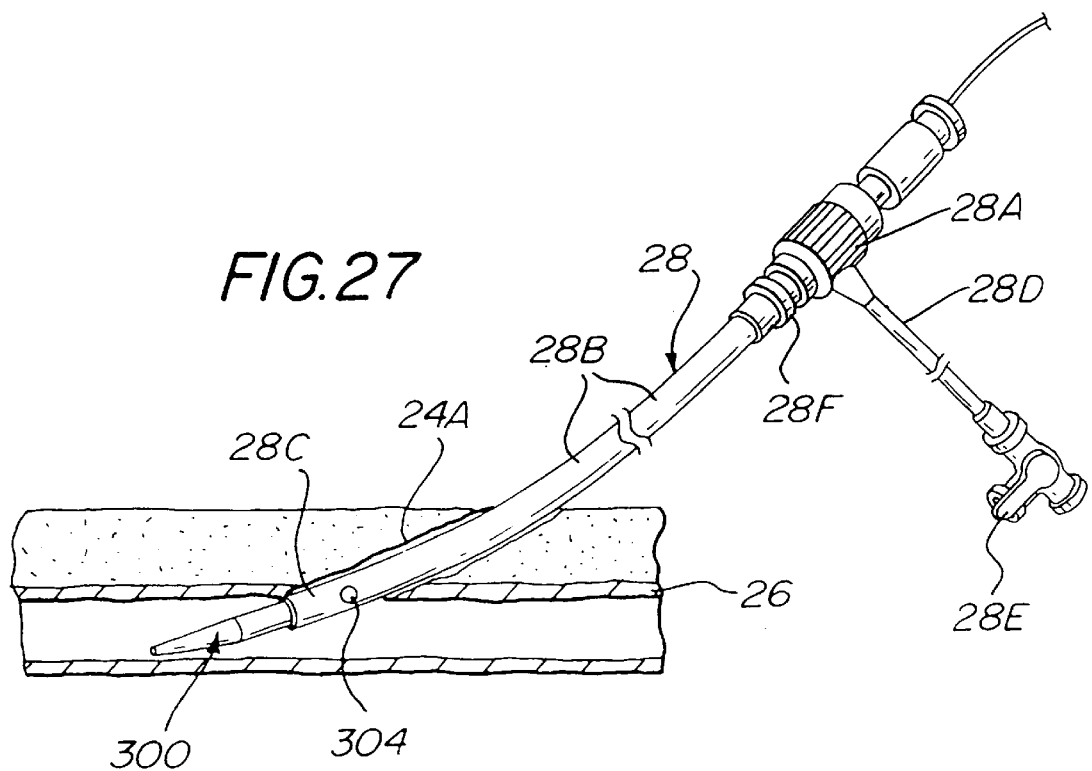
FIG. 27 is an illustration similar to that of FIG. 12 showing desired position of a conventional introducer sheath within the artery as established by the use of the second embodiment of the position indicating device shown in FIG. 26.

In FIG. 26 there is shown a second embodiment of a positioning device 300 for effecting the proper positioning of the introducer sheath 28 within the artery. As can be seen the device 300 basically comprises a conventional obturator whose outer periphery has been modified to include an annular recess 302 extending thereabout. Like the device 200, the device 300 is arranged to be fully inserted within the introducer sheath 28 as shown in FIG. 27. The insertion of the device 300 within the introducer sheath 28 forms an annular passageway between the annular recess 302 of the device 300 and the interior surface of the tubular portion 28B of the sheath 28. A side opening or port 304 is provided in the sidewall 28B of the introducer sheath 28 closely adjacent its open distal end 28C.

The length of the annular recess 302 is selected so that when the device 300 is fully with the introducer sheath 28, and the port 304 in the distal end of the sheath is located within the interior of the artery, the distal end of the annular recess 302 extends just beyond the port 304 while the proximal end of the recess 302 is in fluid communication with the interior of the introducer's sideport 28D.

The port 304 forms a window into which blood in the artery may flow when the distal end 28C of the introducer is located therein. In particular, blood may flow into the window 304 through the annular passageway formed between the recess 302 and the inner surface of the tubular portion 28A of the introducer, into the sideport 28D and from there to the stopcock 28E when the window 304 is within the interior of the artery.

Figure 28:
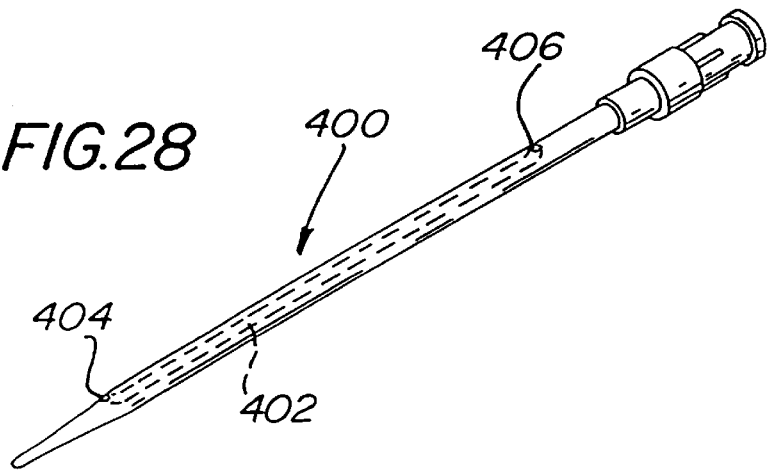
FIG. 28 is an isometric view of a third embodiment of a introducer sheath position indicating device forming a portion of the system of this invention.
Figure 29:
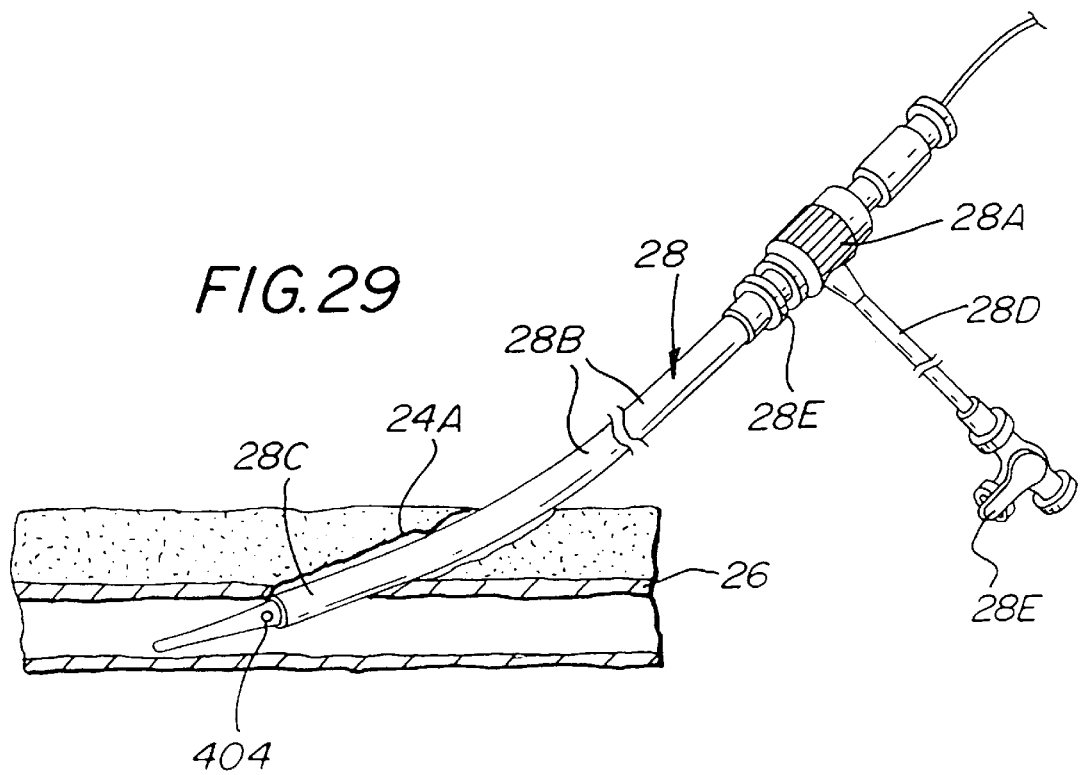
FIG. 29 is an illustration similar to that of FIG. 12 showing desired position of a conventional introducer sheath within the artery as established by the use of the third embodiment of the position indicating device shown in FIG. 28.

In FIG. 28 there is shown a third embodiment of a positioning device 400 for effecting the proper positioning of the introducer sheath 28 within the artery. As can be seen the device 400 basically comprises a conventional obturator having a passageway 402 extending longitudinally down substantially the length of the device. An entrance port 404 extends radially inward into the device communicating with the distal end of the passageway 402, while an outlet port extends radially inward into the device communicating with the proximal end of the passageway 402. Like the devices 200 and 300, the device 400 is arranged to be fully inserted within the introducer sheath 28 as shown in FIG. 29.

The length of the annular passageway 402 is selected so that when the device 400 is fully with the introducer sheath 28 and the distal end of the sheath is located within the interior of the artery, the inlet port 404 of the passageway 402 extends just beyond the free end of the sheath, while the outlet port 406 is in fluid communication with the interior of the introducer's sideport 28D. The port 404 forms a window into which blood in the artery may flow when the distal end 28C of the introducer is located therein.

Figure 30:
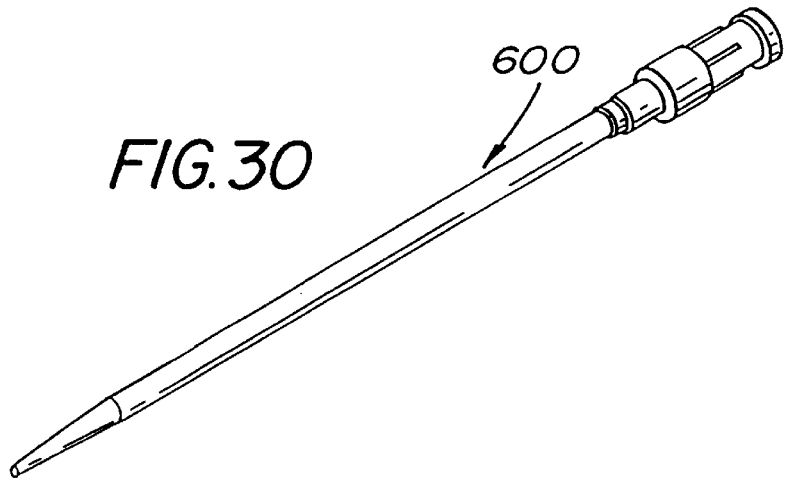
FIG. 30 is an isometric view of a conventional dilator.
Figure 31:
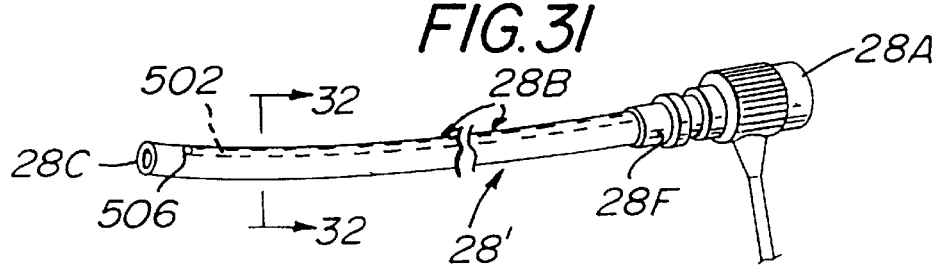
FIG. 31 is an isometric view of a modified introducer sheath forming a position indicating device of the system of this invention.
Figure 32:
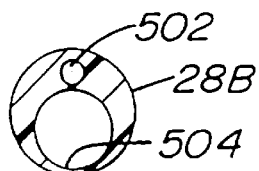
FIG. 32 is an enlarged sectional view taken along line 32—32 of FIG. 31.
Figure 33:
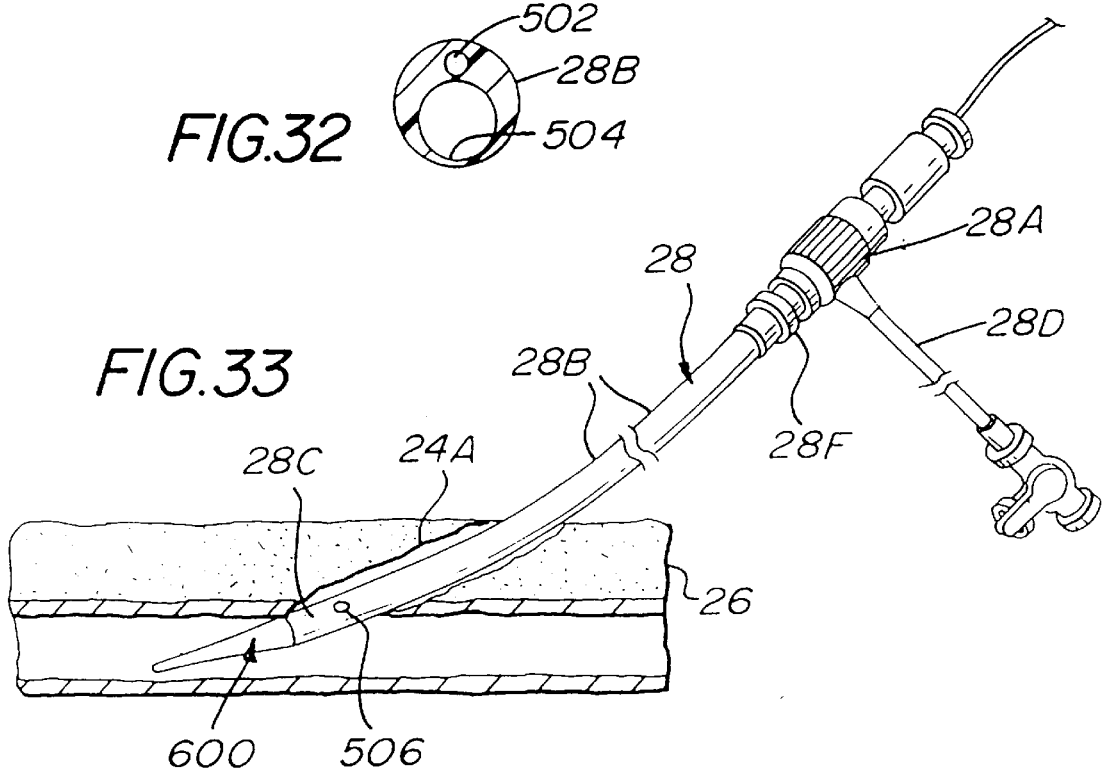
FIG. 33 is an illustration similar to that of FIG. 12 showing desired position of the modified introducer sheath of FIG. 32 located within the artery.

In FIG. 31 there is shown alternative embodiment 28' of an introducer sheath. The sheath is similar to sheath 28 described earlier except that its tubular portion 28B includes a second passageway 502 (FIG. 31) extending therethrough. The passageway 502 serves as the passageway for blood to flow therethrough so that the sheath 28', itself, can act as a positioning device for effecting its proper positioning within the artery. As can be seen in FIG. 31 the passageway 502 extends longitudinally down the sheath 28' within its wall and parallel to the central passageway 504 (the central passageway receives the deployment instrument 20—to be described later). The distal end of the passageway 502 includes a radially extending port 506. The proximal end of the passageway 502 (not shown) is in fluid communication with the interior of the introducer's sideport 28D. The introducer sheath 28' is arranged to be used with a conventional obturator 600 (shown in FIG. 30).

The positioning of the introducer sheath 28 utilizing either of the devices 300 or 400 or the positioning of the introducer sheath 28' utilizing the obturator 600 is similar to that described with reference to the device 200. Thus, after the introducer sheath is positioned as described earlier the stopcock 28E is opened to observe the flow of blood therefrom (thereby indicating that the inlet port or window is within the artery). The introducer sheath is then retracted (moved proximally) until the blood flow through the stopcock just stops, thereby indicating that the distal end 28C of the introducer sheath has just left the artery lumen. The introducer sheath with the device therein is then reinserted approximately 10 mm into the puncture to ensure that the distal end of introducer sheath is at the desired position within the artery. Blood flow should be reestablished through the stopcock at this time. Then the stopcock is closed. From this point the introducer sheath must be kept fixed (as described earlier) and the position indicating device 300 or 400 (or the conventional obturator 600) removed to ready the introducer sheath for receipt of the deployment instrument 20 carrying the closure device 22 through the central passageway in the particular introducer sheath (that passageway is denoted by the reference number 504 in the embodiment 28').

The deployment of the closure will now be described with reference to FIGS. 14–23 and is as follows: The reference detent 108 on the bypass tube is identified by the user and the bypass tube grasped by the user and oriented so that the detent faces up (away from the patient) as shown in FIG. 14. This ensures that the anchor member is located towards the patient. The bypass tube is then inserted into the sheath through the hemostasis valve 28A. The rigid nature of the bypass tube facilitates the passage of the carrier 100 through the hemostasis valve and also protects the closure device from damage. The instrument is then pushed fully down the introducer sheath so that a stop surface 110A on the front (distal) luer fitting 110 (FIG. 11) engages the body of the introducer sheath housing the hemostasis valve. At this time the distal end of the carrier will be in the position shown in FIG. 16 and the anchor member 32 will be located in the artery 26 beyond the distal end of the introducer sheath. The bypass tube 104 remains within the portion of the introducer sheath housing the hemostasis valve 28A.

Figure 17:
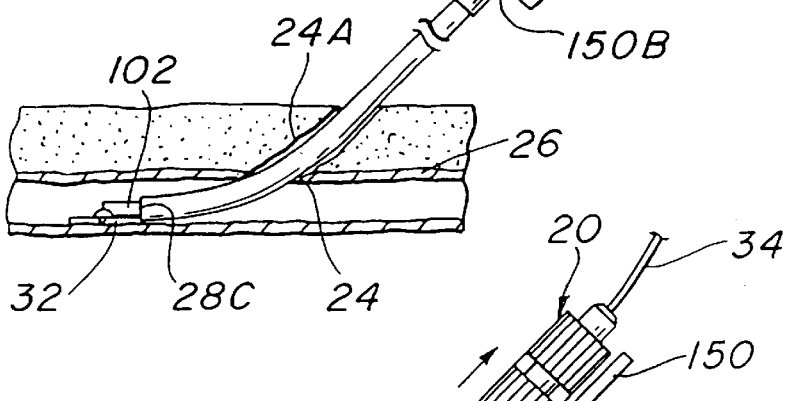
Figure 25:
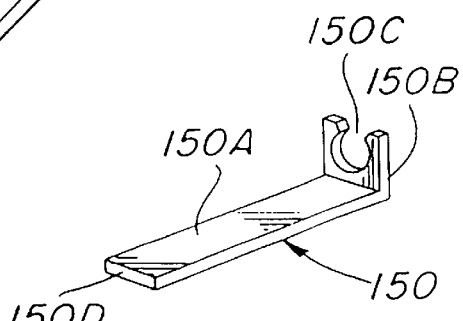
FIG. 25 is an isometric view of a position indicating clip of the system of this invention.

The position indicator clip 150 is then mounted onto the annular recess 28F on the introducer sheath 28 as shown in FIG. 17. As can be seen in FIG. 25 the clip 150 includes a linear section 150A from which a yoke 150B projects perpendicularly. The yoke 150B includes a circular mouth 150C for receipt of the annular recess 28F of the introducer sheath. When mounted in place on the introducer sheath the free end 150D of the indicator clip will extend beyond the distal end of the instrument 20 (beyond the tensioner assembly).

Figure 18:
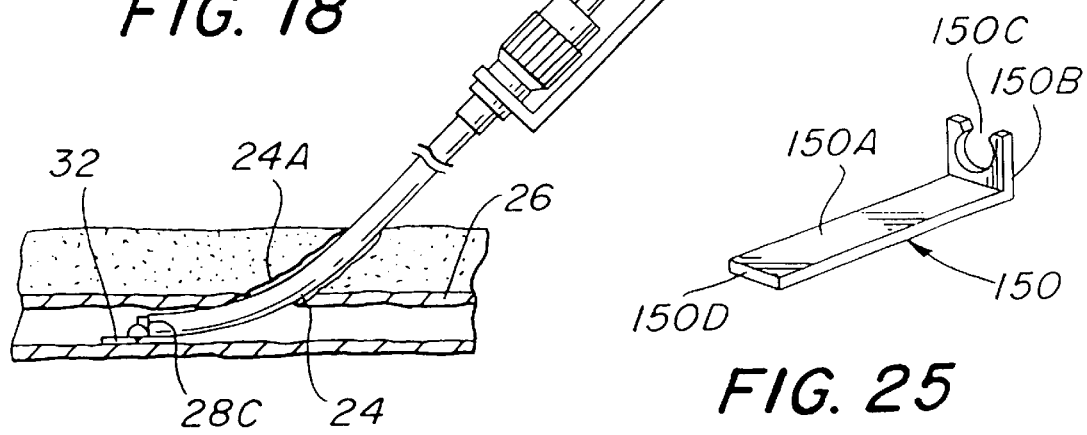

The system 20 is then operated to determine if the anchor member 32 has been properly deployed. To that end the introducer sheath is then held by the user to prevent axial movement and the instrument 20 is carefully withdrawn from it. This action causes the anchor member 32 to engage or catch on to the distal end of the introducer. As the anchor member catches on the distal end of the introducer, resistance will be felt by the user. This resistance must be noted by the time the luer fitting 112 housing the tensioner assembly reaches the free end 150D of the indicator clip 150 as shown in FIG. 18. If so, then the anchor member will have caught on the distal end of the introducer at the location of its hemispherical projection 54 (the desired occurrence).

If, however, no resistance is noted by the time that the luer fitting 112 passes (extends proximally of) the free end of the indicator clip, this will indicate that the anchor has re-entered the introducer sheath, and that the anchor will not catch onto the artery as required. Thus, if no resistance is felt at this point, the instrument 20 must be reinserted within the introducer sheath and the foregoing procedure retried, this time by turning the instrument 20 about its axis 106 by ¼ turns to each side before it is again withdrawn.

If the resistance is felt before the luer fitting reaches the free end of the indicator clip this will indicate that one of the curved ends of the anchor member has caught on the free end of the introducer sheath, an undesired occurrence. Accordingly, the instrument 20 must be withdrawn then reinserted within the introducer sheath and the foregoing procedure retried, this time by turning the instrument 20 about its axis 106 by ¼ turns to each side before it is again withdrawn.

Once the anchor member has been properly deployed, as shown in FIG. 18, the collagen plug is deployed. To that end the introducer sheath 28 and the instrument 20 are held together and withdrawn as a unit from the puncture, whilst swinging the unit toward the vertical as shown in FIG. 19. This action causes the anchor 32 to engage or catch onto the inner surface of the artery 26 contiguous with the puncture 24. The introducer sheath and the instrument are pulled further outward as shown in FIG. 20. Inasmuch as the anchor member is trapped against the interior of the artery wall the continued retraction of the introducer sheath and instrument causes the filament 34 to pull the collagen plug out of the carrier tube 102 and into the puncture tract 24A. As the introducer and instrument come out of the puncture tract, continuous steady resistance will be felt as the tensioner assembly described heretofore controls the force on the filament 34 during the retraction procedure. Continued retraction of the introducer and the instrument brings the tamping member 130 out of the free end of the instrument.

Moreover the pulley arrangement of the filament 24 connecting the anchor member and the plug member ensures that during the retraction of the introducer and the instrument the plug member is moved into engagement with the exterior of the artery wall contiguous with the puncture 24. In fact continued retraction causes the filament to somewhat deform the plug, i.e., cause it to deform radially outward. The existence of blood within the puncture tract further contributes to the deformation of the plug member since the collagen foam expands in the presence of blood.

The retraction procedure continues to pull the introducer and instrument up the filament until the tag 138 is exposed as shown in FIG. 22. At this point the anchor member and collagen plug member have been deployed. At this time the collagen plug is tamped by the tamping member 130. In particular the user quickly compacts the collagen of the plug by gently tensioning the filament by pulling on the introducer sheath and instrument in the proximal direction with one hand. The tamping member is then manually slid down the filament by the user's other hand so that it enters the puncture tract 24A and engages the proximal end of the plug member 32. A few gentle compactions are adequate to achieve the desired result, i.e., to assist the plug member 30 to conform to the artery contiguous with the puncture and to assist to lock the plug in place until hemostasis occurs (which happens very quickly, thereby locking the closure in place). It should be noted that during the tamping action care must be taken to maintain tension on the filament 34 at a load greater than that used on the tamping member 130 to ensure that the tamping action doesn't propel the plug member 30 into the interior of the artery.

After the tamping action is completed the torsion spring 142 is mounted on the filament 34 as shown in FIG. 23. This action is necessary to maintain appropriate tension on the filament while the instrument 20 is removed (the filament severed). In FIGS. 9 and 10 the torsion spring is shown. As can be seen therein the spring 142 includes a pair of legs 142A and 142B projecting outward from a helical central section 142C. Each leg includes a slot 142D at its free end. One of the slots is arranged to receive the filament 34 therein and to engage the tag 138. The other of the slots is arranged to receive the filament 34 therein and to engage the proximal end of the tamping member 130. The legs 142A and 142B are biased by the intermediate section 142C so that when the spring is mounted on the filament as just described they will bias the tamping means towards the plug member 30 to hold it in place so that the filament can be severed (as is necessary to remove the instrument and the introducer from the closure device). Thus, once the spring is in place the filament on the proximal side of the tag 138 is cut and the spring applies a light controlled pressure to the collagen plug and anchor. The closure is left in this condition without being disturbed for approximately 30 minutes. After that time the spring 142 is removed and the filament is then severed at the top of the tamping member 130. The tamping member 130 is then removed and the remaining portion of the filament is taped to the skin at 160 as shown in FIG. 24. The tape (not shown) should be removed and the filament cut subcutaneously prior to the discharge of the patient.

With the closure in final position as shown in FIG. 24 the anchor member 32 (the only portion within the artery) does not take up a substantial portion of the interior of the artery and thus does not block off or otherwise impede the flow of blood therethrough. Since the components of the closure are all formed of resorbable materials the closure can be left in place within the body until it is absorbed.

In FIG. 36 there is shown an alternative embodiment 700 of tamping means constructed in accordance with this invention. The tamping means 700 basically comprises an assembly of two components, whereas the tamping means 130 described earlier is composed of only a single component. Thus, as can be seen in FIG. 36 the assembly 700 comprises a first tubular component 702 and a second tubular component 704. The component 702 includes a central passageway 706 and is formed of any suitable material, e.g., the same material as used to form the tamping component 130 described earlier. The second component 704 also includes a central passageway 708 extending therethrough.

The component 704 is mounted on the front or distal end of the component 702. To that end the component 704 includes an annular recess 710 about its periphery at the proximal end thereof. This recess is arranged to receive the distal end 712 of the component 702, with the two passageways 706 and 708 axially aligned to enable the filament 34 to extend therethrough.

The component 704 is preferably formed of a compressed collagen foam, e.g., the same type of material used for the sealing portion or plug 30 of the closure. The distal end 714 of the component 704 is arranged to engage the plug 30 to tamp it down in the same manner as that accomplished by the distal end 134 of tamping member 130. Once the tamping action is completed the torsion spring 142 is mounted on the filament as shown in FIG. 37 so that it is located between the tag 138 and the proximal end of the component 702 (in the same manner as described with respect to tamping member 130 shown in FIG. 23). Thus, the filament on the proximal side of the tag 138 can be cut, while the spring applies light controlled pressure to the collagen plug 30 and anchor 32. The closure is left in this condition in the same manner as described earlier after which time the spring is removed and the filament severed at the top (proximal end) of the tamping component 702. That component can then be removed, leaving the tamping component 704 within the puncture tract as shown in FIG. 38. The remaining (exteriorly extending) portion of the filament is taped to the skin at 160 as also described earlier.

As should be appreciated by those skilled in the art the two sections of the filament 34 between the anchor component 32 and the plug component 30 effectively form a "pulley" arrangement to increase the mechanical advantage of the force applied to the filament to move the two components toward each other. Accordingly, the closure can be properly seated without the application of a high pulling force. The use of the biased ball and associated seat between which the filament passes during the placing of the closure ensures that irrespective of how hard the instrument and the introducer are withdrawn from the puncture during the deployment and seating of the closure, the amount of force applied to the filament 34, and hence to the closure device, will not exceed a predetermined maximum, e.g., one pound. This feature is of considerable importance to ensure that the anchor portion of the closure is not pulled through the opening (e.g., incision or puncture) once it is in place.

As should also be appreciated from the foregoing, the closure device, the instrument for deploying it, and their method of use enables the ready, effective and efficient sealing of a percutaneous puncture in an artery. Thus, it is expected that the hemostatic puncture closure device 20 will be a significant advancement in the fields of cardiology and radiology. The device may allow continuance of anticoagulation post-procedure, more aggressive use of thrombolytic agents and safer use of large bore catheters. It should also reduce discomfort and complication rates for patients; allow many in-patient procedures to be performed safely on an out-patient basis; decrease the time and cost of interventional procedures; and reduce exposure of hospital personnel to human blood.

Without further elaboration the foregoing will so fully illustrate our invention that others may, by applying current or future knowledge, adopt the same for use under various conditions of service.

What is claimed is:

1. A closure assembly for sealing a percutaneous incision or puncture in the wall of a vessel, duct, lumen or hollow organ in the body of a living being, wherein the incision or puncture includes a tract extending from the opening in the wall of the vessel, duct, lumen or hollow organ to the skin of the being, the tract having an inner surface, said closure assembly comprising a first member formed of a bioabsorbable material and configured for passage through the opening in the vessel, duct, lumen or hollow organ to the interior thereof, a second member arranged to be extended proximally into the tract from said first member and having a greater flexibility than said first member for holding said first member at a desired position within the interior of the vessel, duct, lumen or hollow organ, and a third member separate from said first member and in the form of a mass of a bioabsorbable, material which is arranged for introduction in a first state into the puncture tract without entering into the vessel, duct, lumen or hollow organ and being movable within the tract along said second member relative to said first member when said first member is located within the vessel, duct, lumen or hollow organ, whereupon said third members extends along said second member and proximally of the wall of the vessel, duct, lumen or hollow organ to engage the inner surface of the tract along at least a portion of the length of the tract, said mass being alterable within tract to a second state, wherein said mass in said second state conforms to the shape of the portion of the tract in which it is located and substantially fills that portion of the tract, while cooperating with said first member to seal the incision or puncture from the flow of a fluid therethrough.

2. The closure of claim 1 wherein said third member is alterably deformable to be deformed within the puncture tract to cooperate with said first members to seal the incision or puncture from the flow of fluid therethrough.

3. The closure of claim 1 wherein said third member is formed of collagen and is arranged to be deformed by the application of a tamping force thereto.

4. The closure of claim 1 wherein said first member comprises an anchor and wherein said second member comprises a filament.

5. The closure of claim 3 wherein said first member comprises an anchor and wherein said second member comprises a filament.

6. The closure of claim 4 wherein said second member connects said first and third members in a pulley like arrangement.

7. The closure of claim 5 wherein said second member connects said first and third members in a pulley like arrangement.

8. The closure of claim 1 wherein said first member includes radio-opaque means.

9. The closure of claim 4 wherein said first member includes radio-opaque means.

10. The closure of claim 1 wherein said third member is formed of a hemostatic material.

11. The closure of claim 1 wherein said third member is formed of a material that is alterable from said first state to said second state in response to conditions within the tract.

12. The closure of claim 11 wherein said third member is formed of a material that is alterable from said first state to said second state in response to fluid within the tract.

13. The closure of claim 1 wherein said third member is formed of a material that is alterable from said first state to said second state in response to the application of a mechanical force thereto.

14. The closure of claim 13 wherein said third member is formed of a material that is alterable from said first state to said second state in response to the application of a tamping force thereto.

15. The closure of claim 10 wherein said third member is formed of a material that is alterable from said first state to said second state in response to conditions within the tract.

16. The closure of claim 15 wherein said third member is formed of a material that is alterable from said first state to said second state in response to fluid within the tract.

17. The closure of claim 10 wherein said third member is formed of a material that is alterable from said first state to said second state in response to the application of a mechanical force thereto.

18. The closure of claim 17 wherein said third member is formed of a material that is alterable from said first state to said second state in response to the application of a tamping force thereto.

* * * * *